United States Patent [19]

Moers et al.

[11] Patent Number: 4,736,736

[45] Date of Patent: Apr. 12, 1988

[54] CERVICAL TRACTION ASSEMBLY HAVING HEAD CRADLE WITH OCCIPITAL SHELF

[75] Inventors: John W. Moers, Fallbrook; Richard P. Meyst, Valley Center, both of Calif.

[73] Assignee: 501 Tru-Trac Therapy Products Inc., Temecula, Calif.

[21] Appl. No.: 931,130

[22] Filed: Nov. 17, 1986

[51] Int. Cl.[4] .................... A61F 5/04

[52] U.S. Cl. .................... 128/75; 5/436

[58] Field of Search .................... 128/75, 71, 78, 87 B, 128/84 R; 5/434, 436

[56] References Cited

U.S. PATENT DOCUMENTS

| | | | |
|---|---|---|---|
| 738,283 | 9/1903 | Blomquist . | |
| 921,559 | 5/1909 | McManis et al. | 128/74 |
| 1,242,688 | 10/1917 | Hawley . | |
| 1,936,363 | 11/1933 | Murray | 128/74 |
| 1,984,520 | 12/1934 | Curtis | 128/254 |
| 2,273,088 | 2/1942 | Byers | 128/73 |
| 2,290,040 | 7/1942 | Collins | 128/70 |
| 2,534,587 | 12/1950 | Fisher et al. | 128/71 |
| 2,689,127 | 9/1954 | Silverton et al. | 272/58 |
| 2,703,080 | 3/1955 | Sanders | 128/71 |
| 2,831,482 | 4/1958 | Cobb | 128/84 |
| 3,060,925 | 10/1962 | Honsaker et al. | 128/25 |
| 3,293,667 | 12/1966 | Ohrberg | 5/62 |
| 3,343,180 | 9/1967 | Lothschuetz | 5/434 |
| 3,621,839 | 11/1971 | Barthe | 128/84 R |
| 4,033,339 | 7/1977 | Roberts et al. | 128/73 |
| 4,144,880 | 3/1979 | Daniels | 128/74 |
| 4,154,478 | 5/1979 | Cohune | 297/397 |
| 4,166,459 | 9/1979 | Nightingale | 128/75 |
| 4,218,792 | 8/1980 | Kogan | 5/436 |
| 4,383,713 | 5/1983 | Roston | 5/434 |
| 4,508,109 | 4/1985 | Saunders | 128/75 |
| 4,608,969 | 9/1986 | Hamlin | 128/73 |
| 4,649,905 | 3/1987 | Barnes | 128/74 |

FOREIGN PATENT DOCUMENTS

| | | | |
|---|---|---|---|
| 1538459 | 7/1968 | France | 128/74 |

*Primary Examiner*—Edgar S. Burr
*Assistant Examiner*—Tonya Lamb
*Attorney, Agent, or Firm*—Seiler, Quirk & Tratos

[57] ABSTRACT

An improved cervical traction apparatus comprises a cradle including a bowl-shaped cranial cavity for supporting the head of a user and an occipital shelf support comprising a concave wall extending across the cradle. The cradle is secured on a base assembly which provides for movement of the cradle relative thereto to provide for both independent horizontal and vertical plane movements.

26 Claims, 7 Drawing Sheets

CERVICAL TRACTION ASSEMBLY HAVING HEAD CRADLE WITH OCCIPITAL SHELF

BACKGROUND OF THE INVENTION

A variety of cervical traction apparatus have been proposed. Older devices such as shown in U.S. Pat. No. 2,831,482 utilize head slings which were secured around the patient's chin. These slings or head halters are not only uncomfortable but, during traction, place a substantial amount of force on the chin, sometimes causing discomfort to the patient's temporomandibular joints. Still other traction apparatus allows traction to be centered at the back of the patient's head or in the occipital area such as described in U.S. Pat. Nos. 4,166,459 and 4,508,109. However, such prior devices do not provide for sufficient flexibility in the angular placement and location of the patient's head during supine traction where variation about both horizontal and vertical axes is desirable or important in the traction therapy. Thus, for example, although the apparatus in U.S. Pat. No. 4,508,109 provides for "side bending" whereby the patient's head is angled about a generally vertical axis to achieve "unilateral" traction, the apparatus carriage is not movable or rotatable about a horizontal axis for spinal axis rotation. It is to the improvement of such cervical traction apparatus in providing not only horizontal plane traction angles but also spinal axis rotation angles in a vertical plane that the present invention is directed.

SUMMARY OF THE INVENTION

The improved cervical traction apparatus comprises a cradle for receiving the head of a patient in which is formed a bowl-shaped cranial cavity and an occipital shelf support, the patient's head being received in the cavity while the occipital shelf support is positioned adjacent to the occipital bone. The cradle is supported on a movable base assembly which is securable at any desired angle in a horizontal plane to provide for side bending. In addition, the cradle is provided with slots in which slot engaging members secured on the base assembly allow the cradle to be rotated on the spinal axis to any desired angle in a vertical plane. Such means provides for total flexibility in allowing a physician or therapist to comfortably rest the patient's head in a cradle while allowing the cradle to be positioned at any desirable angle relative to the patient's spine for cervical traction therapy.

DETAILED DESCRIPTION OF THE INVENTION

Figure 1:
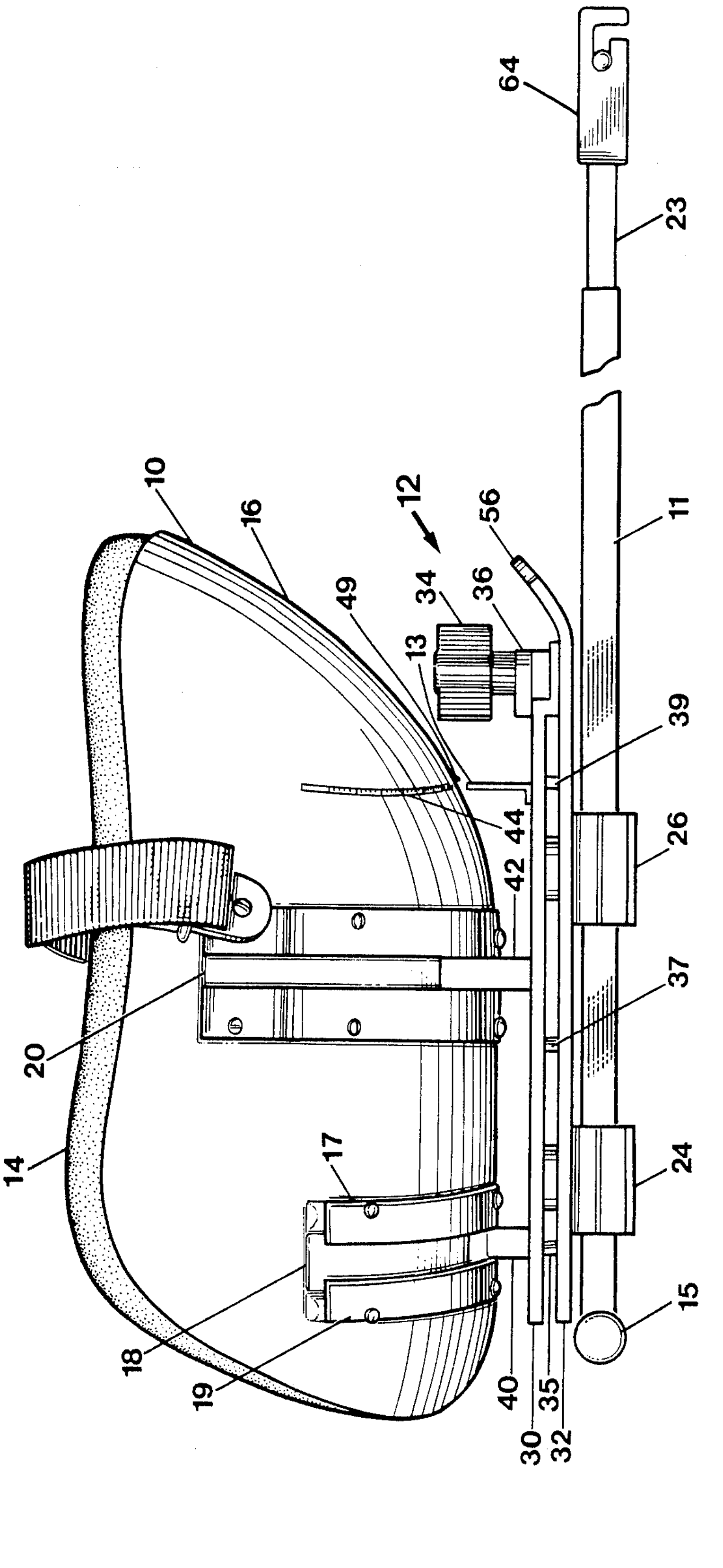
FIG. 1 is a side view of the improved cervical traction apparatus showing the cradle and base support assembly.

In FIG. 1 there is shown the cervical traction apparatus of the invention. The basic apparatus includes a cradle assembly 10 which is mounted on a base assembly 12. The cradle assembly comprises a cushion 14 mounted in a supporting shell 16. The base assembly includes an upper base member or plate 30 and a lower base member 32. A pivot pin 35 is secured between the two plates whereby upper plate 30 may be pivoted or rotated horizontally with respect to lower plate 32 about the pivot pin. The two plates are also held apart or maintained in spacial relationship using spacers 37 and 39, each shown secured to the bottom of upper plate 30, although they could be secured instead to the top surface of lower plate 32. Such spacers are made of a self-lubricating thermoplastic material to facilitate smooth operation. Other means for supporting the spaced plates may be used.

Lower plate 32 is secured along track 11 by a pair of slides 24 and 26. The slides include self-lubricating inserts to assure that the friction force of moving the cradle along the track does not appreciably affect traction forces applied to the base assembly and thence to the patient. The slides are secured to the bottom surface of lower plate 32 and slidably engage track 11 so that the base assembly and cradle may be moved along the track. Such a feature is important since the patient's head will rest in the cushion of the cradle assembly and the base assembly will be pulled or urged in the direction of the traction means, for example, a traction machine or weights and pulleys. Such a relationship is illustrated further in FIG. 6 and will be explained in more detail hereinafter. One end of the track 11 is secured to a post or traction machine while the other end is supported on a base leg 15 which rests on a table or the like. The track also preferably includes telescoping track portion 23 which will allow the track to be lengthened or shortened as desired, which feature is especially desirable to accommodate different traction machines and/or table elevations. The track portion 23 conveniently slides within larger track portion 11 and may be provided with a locking detent or pin to prevent portion 23 from being entirely removed or separated from the track.

Cradle assembly 10 is supported on the base assembly by a plurality of slot engaging fittings 40 and 42. In such a device, any number of such fittings may be used. In the apparatus shown three are used although from the side view in FIG. 1 only two are visible, the third fitting being located behind fitting 42. These fittings are fixed on upper base plate 30 and are engaged in channels 18 and 20 formed in shell 16 of the cradle. Slot guides 17 and 19 cover a portion of each channel 18 and 20 which guides extend over flanges of the slot engaging fittings to hold them in place. These fittings and channels allow the cradle to be rotated about a patient's spinal axis independently of the horizontal plane rotation of plate 30 relative to plate 32. Other means for providing the same movement of the cradle along the spinal axis may be used, and the specific means including the fittings and channels as described above and shown in the drawings is by example only. Moreover, in the embodiment shown, the number of the channels and fittings used may be varied depending on the desired support of the cradle on the base assembly.

To provide indexing and more precise angular alignment of the patient's head relative to a vertical axis in side bending or unilateral traction, as well as to secure the cradle in the desired position once it is achieved, a friction fitting 36 is tightened against upper plate 30 utilizing a thumb screw 34 threadedly engaging the lower plate 32. Observing also FIG. 5, upper plate 30 is provided with a horizontal deflection scale 38 for informing a therapist of the cradle angle of deflection relative to track 11, in the horizontal plane. For example, such a scale may conveniently be provided with angles of ±25° from center or zero. To indicate the angle of vertical plane deflection, i.e., spinal axis rotation, a vertical deflection scale on panel 13 may be used. A pointer or index mark 49 formed on shell 16 will assist an operator in setting a suitable vertical deflection. Alternatively, a scale 44 may be provided on the shell for the same purpose. Of course, other means for showing and selecting a desirable angle deflection both along the horizontal and vertical axes may be provided.

Figure 2:
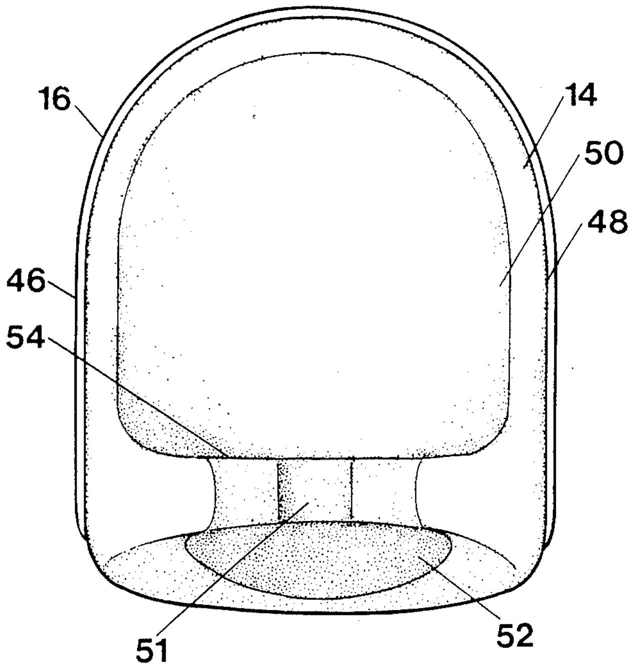
FIG. 2 is a top view of the cradle.
Figure 3:
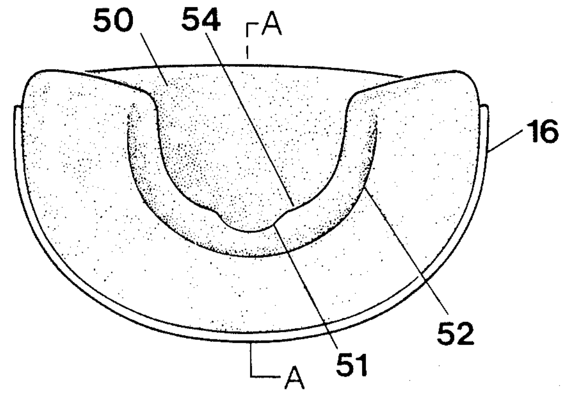
FIG. 3 is a front view of the cradle.

An important feature of the apparatus of the invention is the shape of the cradle shown in FIGS. 2 and 3. In the preferred embodiment, the cradle assembly includes a rigid shell 16, also shown in sectional view in FIG. 4, and a cushion 14 supported within the bowl-shaped shell. The shape of the cushion is particularly important and includes a bowl-shaped surface 50 for supporting the head of a user and on which the back of the patient's head rests, and an occipital shelf support 54 extending across between the sides 46 and 48 of the cradle. The concave wall of the occipital shelf support is arc-shaped particularly shown in FIG. 3 which arc is substantially parallel with the arc-shape of the bowl 50 although the the upper surface of the shelf is not as deep as the surface of the bowl. The preferred cradle also includes a extension insert shelf 52, also arc-shaped, its surface also being substantially parallel with the arc-shaped surface of occipital shelf support 54. The occipital shelf support also preferably includes a recess or depression 51 to allow clearance for the spinal bone protrusion. The material of which the cushion is made may be any composition comfortable to a patient. Such cushion is preferably removable from the shell and may comprise a disposable hygienic insert. Conveniently, foamed plastics are useful, and foamed self-skinning polyurethane is most preferred.

In use, the patient's head will be placed in the cradle cushion so that the back of the cranium rests in the bowl 50 with the occipital bone resting on occipital shelf support 54. In this manner, as the cradle is pulled or urged by traction with base assembly 12 sliding along track 11, the patient's head is urged in the direction of the traction and away from the patient's body which is lying on a conventional traction table or the like. The patient's neck may also rest on an extension insert 57, shown in FIGS. 10 and 11, so that the neck portion of the patient is supported in a position to cause the cervical spine to be placed in a condition of extension. Varying sizes of such extension inserts may be used to create various degrees of extension. The extension inserts may be glued, taped or otherwise removably secured in position on the extension insert shelf 52.

Figure 4:
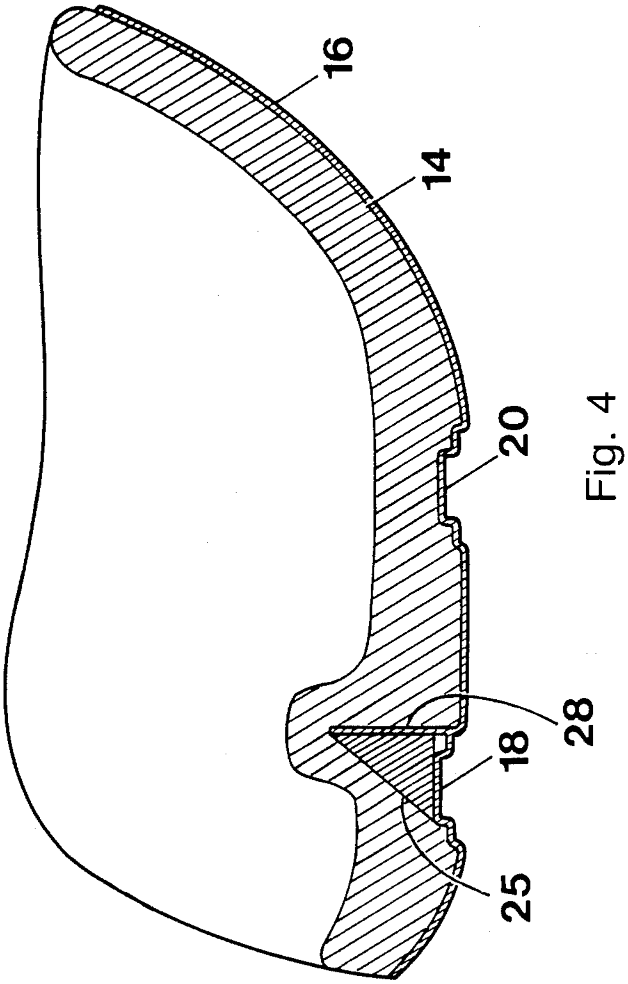
FIG. 4 is a side sectional view of the cradle taken along lines A—A of FIG. 3.

In FIG. 4 shell 16 is illustrated more particularly. On the outside of the shell are two channels 18 and 20 for receiving the slot engaging fittings as illustrated in FIG. 1. Interiorly of the shell is an occipital shelf support which includes a rib 28 extending the width of the shell and a plurality of reinforcing members 25 secured to and spaced along the rib (only one being seen in the side view of FIG. 4). Cushion 14 is supported in the shell, the bottom exterior surface of the cushion being shaped and formed so that it fits into channels 18 and 20 formed into the shell, including slots and depressions beneath the occipital shelf support for receiving rib 28 and reinforcing members 25.

Figure 5:
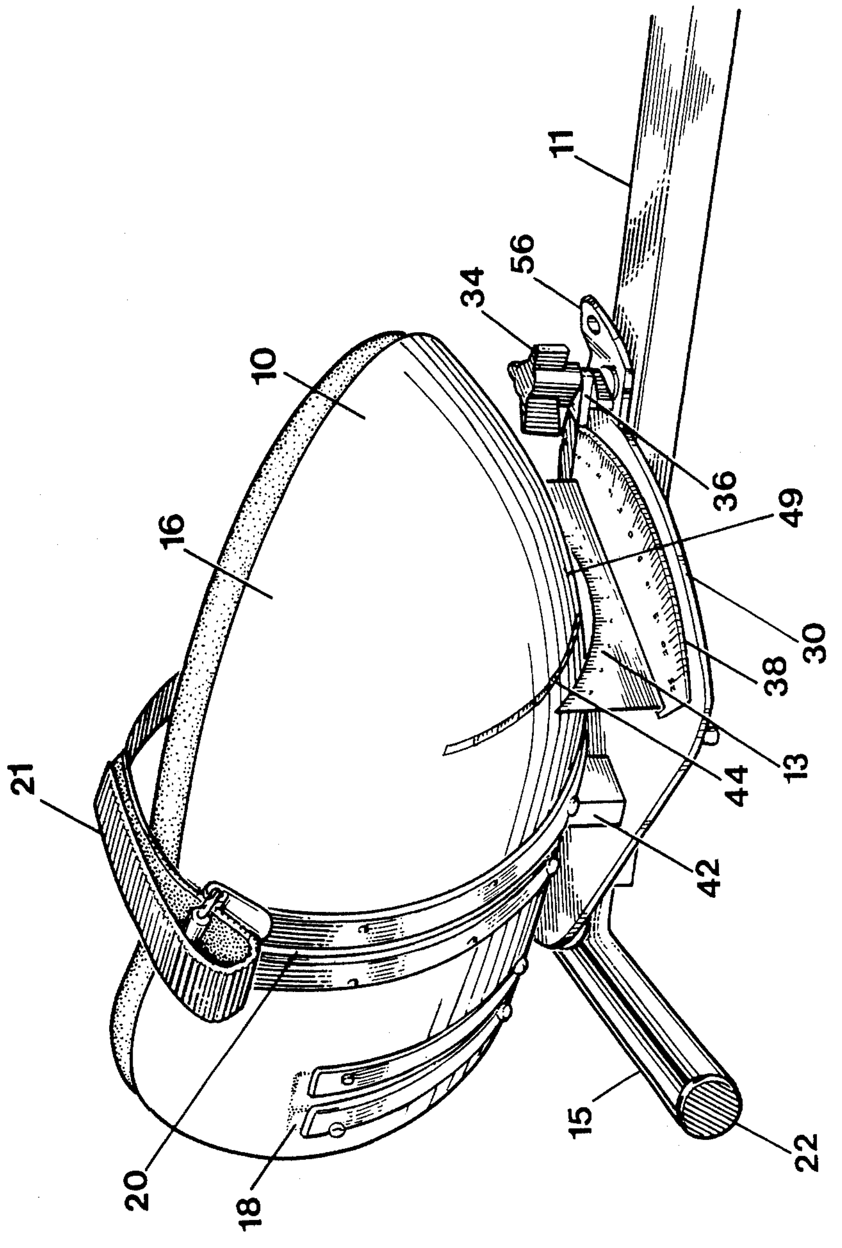
FIG. 5 is a perspective view of the cradle and base support assembly components.

In FIG. 5 is a view illustrating the angular placement of the cradle relative to the base and the direction of traction in achieving advantage of the apparatus. As shown, cradle assembly 10 has been rotated along the spinal axis by moving the assembly on the slot engaging fittings, only fitting 42 being visible in the drawing. This angular movement tilts the cradle assembly about the spinal axis to give a desired spinal axis rotation which may be observed on vertical deflection scale 44 located on panel 13 relative to an index mark 49 conveniently located on the lower surface of the shell. The alternative index 44 secured on the shell is also shown. The cradle assembly shown has also been deflected in a horizontal plane wherein upper base plate 30 is offset relative to the lower base plate (not shown). This deflection may be observed on horizontal deflection scale 38 relative to friction and indexing fitting 36. The cradle assembly shown also includes a head strap 21 conveniently secured to the shell 16. The head strap may be adjustable using "Velcro" or the like for comfortably assisting in securing the patient's head in the cradle. A pull hanger 56 is attached to lower base plate 32 as more particularly seen in FIG. 1. The pull hanger is provided with a hole or other means for securing a pulley or traction cord the other end of which is attached to weights or a traction machine. In another embodiment shown in FIG. 5, base leg 15 may be provided with a roller 22 at each end to assist in moving the apparatus on a traction table.

Figure 6:
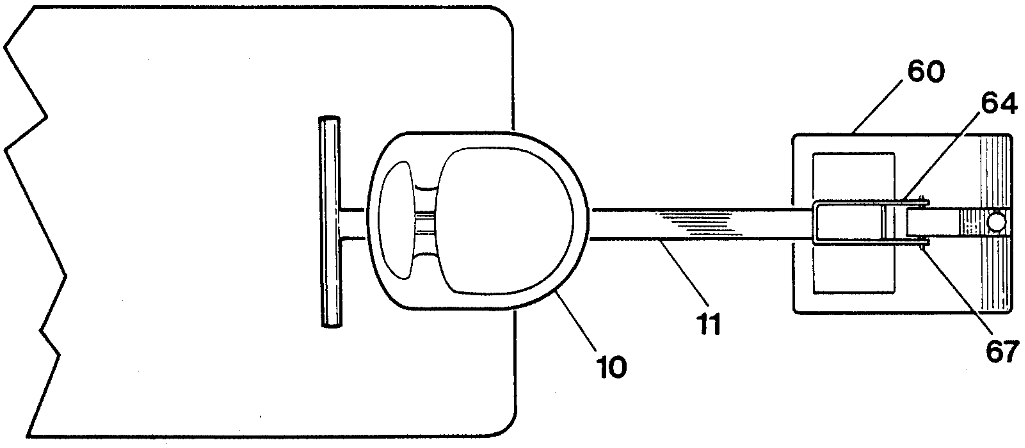
FIG. 6 illustrates means for securing the cervical traction apparatus to a traction machine.
Figure 7:
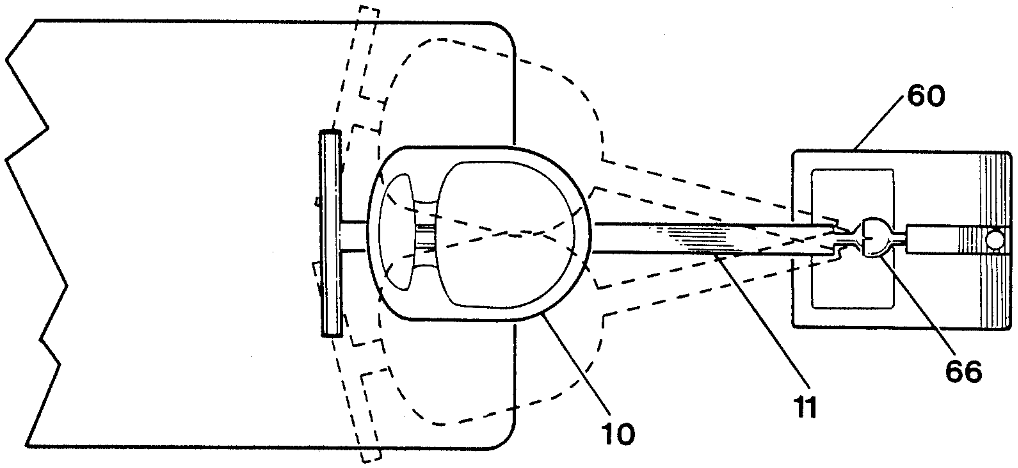
FIG. 7 illustrates an improved universal connection member.

In FIGS. 6 and 7 there are shown examples of alternative means for securing the apparatus of the invention to a traction machine. In FIG. 6, a conventional device 64, also seen in FIG. 1, secured to the end of track 11, is attached to traction machine 60 via projecting members 67. As will be evident, because the device has no independent movement from the track, there are no angular variations available between the track and the traction machine other than vertically. On the other hand, in an embodiment shown in FIG. 7, a universal joint 66 in the form of a ball-in-socket means at the end of track 11 connects the track to traction machine 60. Such a universal-type joint allows substantially greater flexibility in positioning the apparatus of the invention relative to such a traction machine and/or to the traction table or the like on which the apparatus rests as illustrated by the phantom representations of the apparatus.

Figure 8:
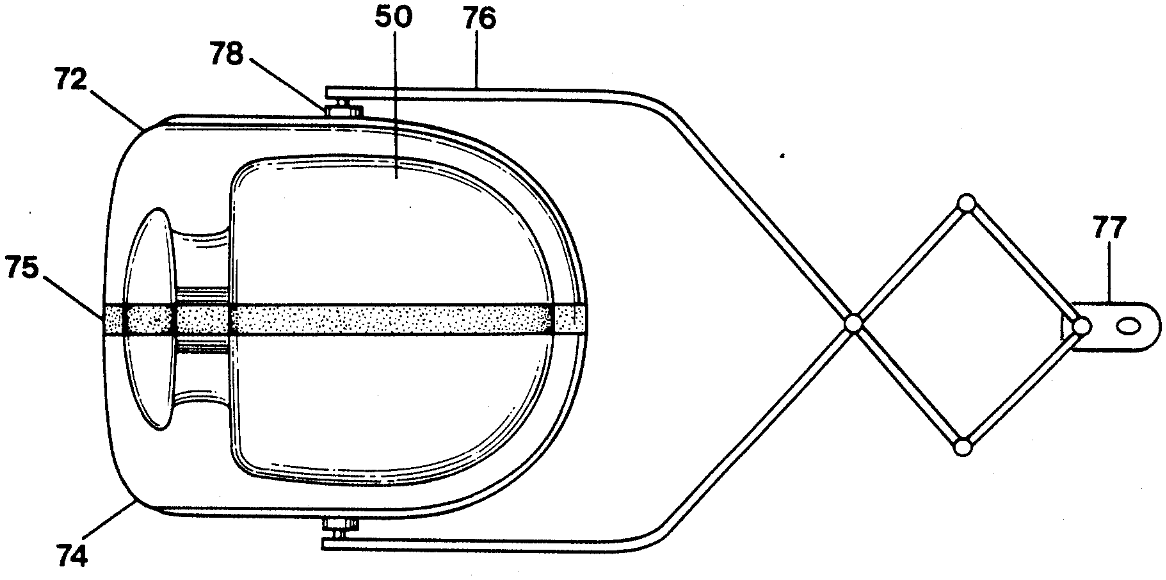
FIG. 8 illustrates a modified expandable cradle embodiment.

In FIG. 8 there is shown yet another embodiment of the apparatus invention comprising a split cradle made up of two opposite cradle halves or portions 72 and 74. A spacer material 75 offers padding and is a filler for the space between the cradle halves. Such a cradle embodiment allows the apparatus to be used for more snugly fitting the head of a user as the cradle portions are urged together. This movement and adjustment of the cradle half portions may be assisted utilizing a tong or scissor-like device 76 secured on hinges 78 on each side of the cradle. A pull hanger 77 may be secured to the other end of the apparatus as shown. Such tong or scissor-like device would, as a result of a traction force being applied to the hanger 77, apply continuing side forces upon the patient's head to maintain proper contact and positioning.

Figure 9:
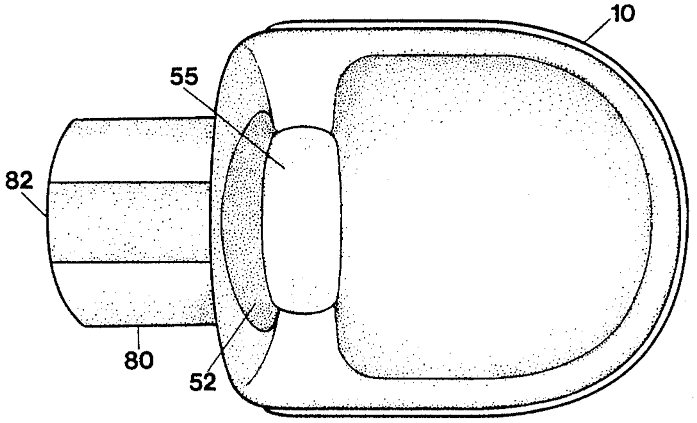
FIG. 9 is a view of the cradle shown in FIG. 2 showing an optional vertebrae immobilizer attachment and neck supporting insert.

In FIG. 9 there is shown still another embodiment for the cradle assembly of the invention comprising a vertebrae immobilizer extension 80 having a channel 82 for receiving spinal vertebrae when the patient's head is placed in the cradle. Such an extension may be bolted, screwed or otherwise attached to the base assembly 12 of FIG. 1 or to the cradle shell and will assist in immobilizing the desired vertebrae during traction.

Figure 10:
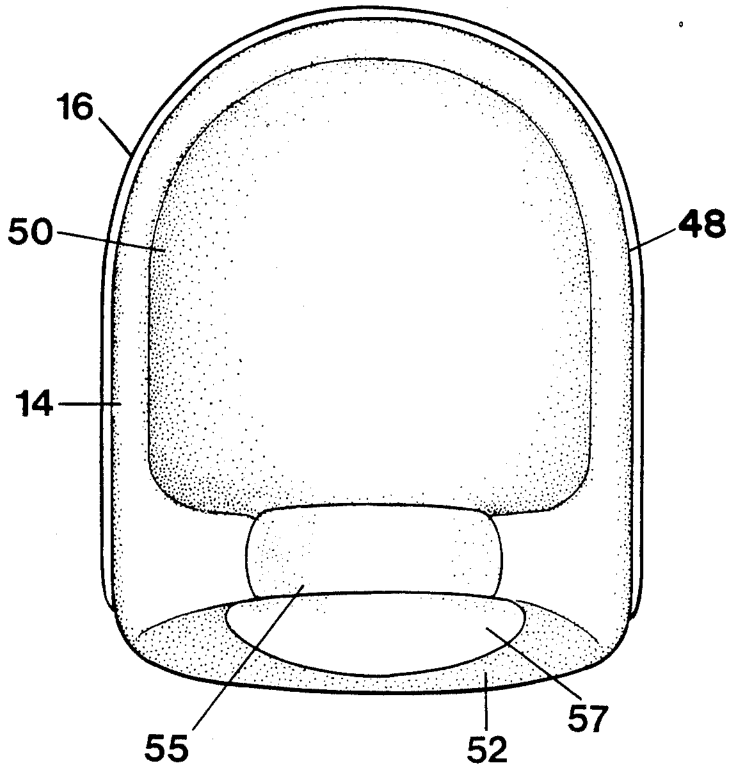
FIGS. 10 and 11 are top and front views, respectively, showing the cradle and optional neck supporting inserts.
Figure 11:
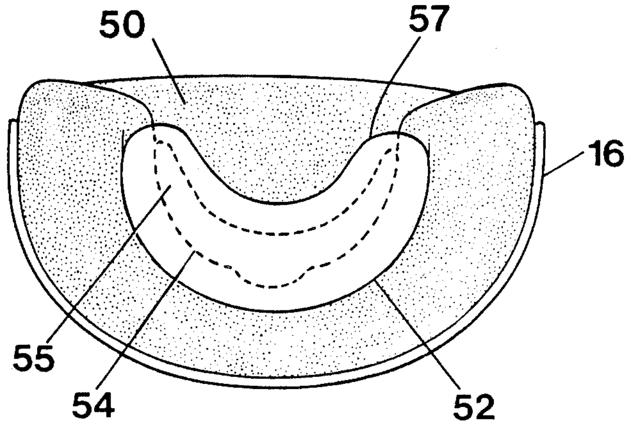

In FIGS. 9–11 there is also illustrated an optional occipital insert 55 for accommodating patients having different head and/or neck sizes and shapes. A suitable occiptal insert is preferably made of a foam plastic material that may be removably secured to the cushion on the surface of occipital shelf 54. The occipital inserts may be of different sizes and shapes to fit different patient needs, especially useful where the cushion shown in FIGS. 2 and 3 is simply not adequately supportive. The inserts may be glued, taped, or otherwise removably secured on the cushion.

The specific components of the apparatus shown in the drawings and described herein are by way of example only and are not intended to be limiting to the scope of the invention recited in the following claims.

I claim:

1. In a cervical traction apparatus the improvement comprising a cradle for supporting the head of a user having a top end and a bottom end and opposite sides extending therebetween, said cradle including (a) an occipital shelf comprising a concave wall extending across said cradle between said opposite sides and having an upper surface of a first depth for supporting an occipital bone, (b) a concave cranial cavity having a surface of a second depth for supporting the head of a user defined between said top end and opposite sides of said cradle and said occipital shelf, and (c) an extension insert shelf extending between said occipital shelf and said bottom end and having a surface of a third depth, and wherein said first depth of said upper surface of said occipital shelf is less than said second depth of said surface of said cavity and said third depth of said surface of said extension insert shelf.

2. The apparatus of claim 1 including an extension insert removably secured on said extension insert shelf.

3. The apparatus of claim 1 wherein said occipital shelf includes a recess for receiving a spinal bone protrusion.

4. The apparatus of claim 1 wherein said extension insert shelf comprises an arc-shaped depression extending between said opposite sides.

5. The apparatus of claim 4 wherein said occipital shelf is arc-shaped and substantially parallel with said extension insert shelf.

6. The apparatus of claim 1 wherein said cradle comprises a rigid concave shell portion and a separate, cushioned head support portion removably received in said shell portion, and wherein said occipital shelf, said cranial cavity and said extension insert shelf are formed in said head support portion.

7. The apparatus of claim 6 wherein said shell portion includes a rib member for supporting said occipital shelf.

8. The apparatus of claim 6 including a separate vertebrae extension immobilizer member removably secured to said shell portion.

9. The apparatus of claim 6 wherein said head support portion comprises foamed plastic.

10. The apparatus of claim 9 wherein said foamed plastic comprises self-skinning urethane.

11. The apparatus of claim 6 including an occipital support insert removably secured on said head support portion.

12. The apparatus of claim 11 wherein said occipital support insert is secured on said occipital shelf.

13. The apparatus of claim 1 including a base assembly having first positioning means for selectively aligning said cradle about a vertical axis and second positioning means for selectively aligning said cradle about a horizontal axis generally parallel to the spinal axis.

14. The apparatus of claim 13 including a separate vertebrae extension immobilizer member removably secured to said base assembly.

15. The apparatus of claim 13 wherein said second positioning means comprises slot means along the exterior of said cradle and slot engaging means movably secured in said slot means whereby said cradle is movable relative to said slot engaging means.

16. The apparatus of claim 13 wherein said first positioning means comprises an upper base member and a lower base member, said cradle being secured to said upper base member and wherein said upper base member is horizontally movable relative to said lower base member.

17. The apparatus of claim 16 wherein said upper base member is pivotally mounted on said lower base member.

18. The apparatus of claim 16 including a track and wherein said lower base member is slidably attached thereto.

19. The apparatus of claim 18 wherein said track includes a telescoping portion.

20. The apparatus of claim 18 including a ball-in-socket member or universal joint secured adjacent one end of said track.

21. The apparatus of claim 16 wherein said second positioning means comprises exterior slot means on said cradle and slot engaging means movably secured in said slot means, said slot engaging means being secured on said upper base member whereby said cradle is movable about a vertical axis by moving said upper base member relative to said lower base member and movable about a horizontal axis by moving said cradle along said slot means relative to said slot engaging means.

22. The apparatus of claim 21 including a first deflection scale cooperating with said first positioning means for indicating an angle of horizontal deflection of said cradle for horizontal side bending.

23. The apparatus of claim 22 wherein said deflection scale is secured on said upper base member.

24. The apparatus of claim 21 including a second deflection scale cooperating with said second positioning means for indicating an angle of vertical deflection of said cradle relative to the spinal axis of a user.

25. The apparatus of claim 24 wherein said second deflection scale is secured on said cradle.

26. The apparatus of claim 24 wherein said second deflection scale is secured on said upper base member.

* * * * *